(12) United States Patent
Kitajima et al.

(10) Patent No.: US 7,375,537 B2
(45) Date of Patent: May 20, 2008

(54) METHOD AND APPARATUS FOR MEASURING RELATIVE DIELECTRIC CONSTANT

(75) Inventors: Toshikazu Kitajima, Kyoto (JP); Motohiro Kono, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 454 days.

(21) Appl. No.: 11/087,572

(22) Filed: Mar. 24, 2005

(65) Prior Publication Data

US 2005/0239224 A1    Oct. 27, 2005

(30) Foreign Application Priority Data

Apr. 26, 2004    (JP)    ............... 2004-129480

(51) Int. Cl.
*G01R 27/26*    (2006.01)
(52) U.S. Cl. .................... 324/671; 324/662
(58) Field of Classification Search .......... 324/671, 324/662
See application file for complete search history.

(56) References Cited

U.S. PATENT DOCUMENTS

| | | | |
|---|---|---|---|
| 4,812,756 A | 3/1989 | Curtis et al. | |
| 5,225,690 A * | 7/1993 | Sakai et al. | ............ 250/559.09 |
| 5,485,091 A | 1/1996 | Verkuil | |
| 6,597,193 B2 | 7/2003 | Lagowski et al. | |
| 6,915,232 B2 * | 7/2005 | Kitajima et al. | ............ 702/171 |

FOREIGN PATENT DOCUMENTS

| | | |
|---|---|---|
| JP | 4-132236 | 5/1992 |
| JP | 2001-332596 A | 11/2001 |
| JP | 2003-98073 A | 4/2003 |

OTHER PUBLICATIONS

Miller, Tom, G. "A New Approach for Measuring Oxide Thickness." Semiconductor International, Jul. 1995, pp. 147-148.

* cited by examiner

*Primary Examiner*—Andrew H Hirshfeld
*Assistant Examiner*—Amy He
(74) *Attorney, Agent, or Firm*—McDermott Will & Emery LLP

(57) ABSTRACT

A relative-dielectric-constant measuring apparatus according to the present invention includes an ellipsometer and a capacitance measuring part. The ellipsometer allows non-contact measurements of the film thickness and optical constants of an insulation film formed on the upper surface of a wafer. The capacitance measuring part, on the other hand, allows non-contact measurements of the gap between the insulation film and an electrode and accumulation capacitance. The relative-dielectric-constant measuring apparatus can calculate the relative dielectric constant of the insulation film based on the measured film thickness, gap, and accumulation capacitance. Thus, the relative dielectric constant of the insulation film can be determined without contact and with high precision.

13 Claims, 6 Drawing Sheets

METHOD AND APPARATUS FOR MEASURING RELATIVE DIELECTRIC CONSTANT

BACKGROUND OF THE INVENTION

1. Field of the Invention

The present invention relates to a relative-dielectric-constant measuring method and apparatus for measuring the relative dielectric constant of an insulation film formed on the surface of a substrate.

2. Description of the Background Art

One of the most difficult issues associated with finer interconnections in semiconductor devices is the process of interconnecting electronic circuits. A problem with finer interconnections in semiconductor devices is a time delay of electric signals. Thus, in recent years progress has been made in multilevel interconnect technology.

Between two multilevel interconnect lines, an interlayer insulation film (hereinafter simply referred to as an "insulation film") is buried. The insulation film is evaluated from its various physical properties such as insulating properties, mechanical strength, thermal resistance, and relative dielectric constant. Among these, the most important physical property is the relative dielectric constant. The insulation film is desirable to have a low relative dielectric constant for device operation. However, it is known that damages caused to the insulation film by processes such as etching will increase the relative dielectric constant of the insulation film. Thus, the material for the insulation film is selected also from the viewpoint of easy processing and leakage properties, and on the other hand, a technique for measuring the relative dielectric constant of an insulation film becomes important.

As techniques for measuring the relative dielectric constant of an insulation film, for example, there are known a technique for forming a metal electrode on the surface of an insulation film, and a technique for bringing a metal probe into contact with the surface of an insulation film.

However, the technique for forming a metal electrode on the surface of an insulation film might cause changes in the properties of an insulation film due to heat generated during electrode formation, and the like. Also, this technique is destructive measurement, so the measurement is time-consuming.

On the other hand, the technique for bringing a metal probe into contact with the surface of an insulation film provides contact between the metal probe and the surface of an insulation film by way of a liquid metal such as mercury. Thus, there is no need to form a metal electrode on the surface of the insulation film, thus allowing easy and simple measurement. However, high-precision measurement is difficult because of an unstable contact area of mercury. Besides, the use of mercury that is harmful to the human body is also a problem.

In order to solve the aforementioned problems, non-contact measurement of the relative dielectric constant of an insulation film is desirable. As a technique for non-contact measurement of the relative dielectric constant of an insulation film, there is known a technique for applying charge to the surface of an insulation film by corona charging and then obtaining surface charge and potential at that time, thereby to obtain the relative dielectric constant of the insulation film. However, since the insulation film generally has a porous structure to reduce its relative dielectric constant, a large amount of charge applied to the surface of the insulation film will leak into the film. Thus, it is difficult to accurately calculate the relative dielectric constant of an insulation film through analysis that is based on the assumption that charge exists only on the surface of the insulation film.

That is, using either of the aforementioned measurement techniques involves difficulty in non-contact and accurate measurement of the relative dielectric constant of an insulation film.

SUMMARY OF THE INVENTION

The present invention is directed to a relative-dielectric-constant measuring method for measuring the relative dielectric constant of an insulation film formed on the surface of a substrate.

According to the present invention, the relative-dielectric-constant measuring method includes the steps of: (a) measuring a film thickness of the insulation film without contact; (b) measuring a gap between the insulation film and an electrode which is spaced as opposed to the insulation film; (c) measuring an accumulation capacitance between the substrate and the electrode; and (d) calculating the relative dielectric constant of the insulation film based on the film thickness measured in the step (a), the gap measured in the step (b), and the accumulation capacitance measured in the step (c).

The film thickness of the insulation film can be measured without contact. Also, the gap and the accumulation capacitance can be measured without contact. Then, the relative dielectric constant of the insulation film can be calculated based on the measured film thickness, gap, and accumulation capacitance. This allows non-contact and accurate measurement of the relative dielectric constant of the insulation film.

Preferably, the method further includes the step of (e) measuring optical constants of the insulation film without contact. In the step (b), the gap is measured based on the optical constants measured in the step (e).

Even for an insulation film with unknown optical constants, the optical constants can be measured without contact. Then, the gap can be measured with high precision by using the measured optical constants.

Preferably, in the step (e), the optical constants of the insulation film are measured by ellipsometry.

The ellipsometry allows fine measurement of the optical constants of the insulation film.

Preferably, in the step (b), the gap is measured based on the amount of a laser beam that is completely reflected by an optical member to which the electrode is secured. Also, the ellipsometry in the step (e) uses a measuring light of the same wavelength as the laser beam.

The gap can be measured using the optical constants corresponding to the wavelength of the laser beam. This allows more accurate gap measurement.

Preferably, in the step (a), the film thickness of the insulation film is measured by ellipsometry.

The ellipsometry allows fine measurement of the film thickness of the insulation film.

Preferably, the method further includes the step of (f) adjusting the gap. The steps (f), (b), and (c) are repeated a plurality of number of times to obtain a plurality of sets of measurement results of the gap and the accumulation capacitance. In the step (d), the relative dielectric constant of the insulation film is calculated based on the plurality of sets of measurement results.

This allows more accurate measurement of the relative dielectric constant of the insulation film.

The present invention is also directed to a relative-dielectric-constant measuring apparatus.

Thus, an object of the present invention is to provide a technique for measuring the relative dielectric constant of an insulation film without contact and with high precision.

These and other objects, features, aspects and advantages of the present invention will become more apparent from the following detailed description of the present invention when taken in conjunction with the accompanying drawings.

DESCRIPTION OF THE PREFERRED EMBODIMENTS

Hereinbelow, a preferred embodiment of the present invention is described.

<1. General Structure of Relative-Dielectric-Constant Measuring Apparatus 1>

Figure 1:
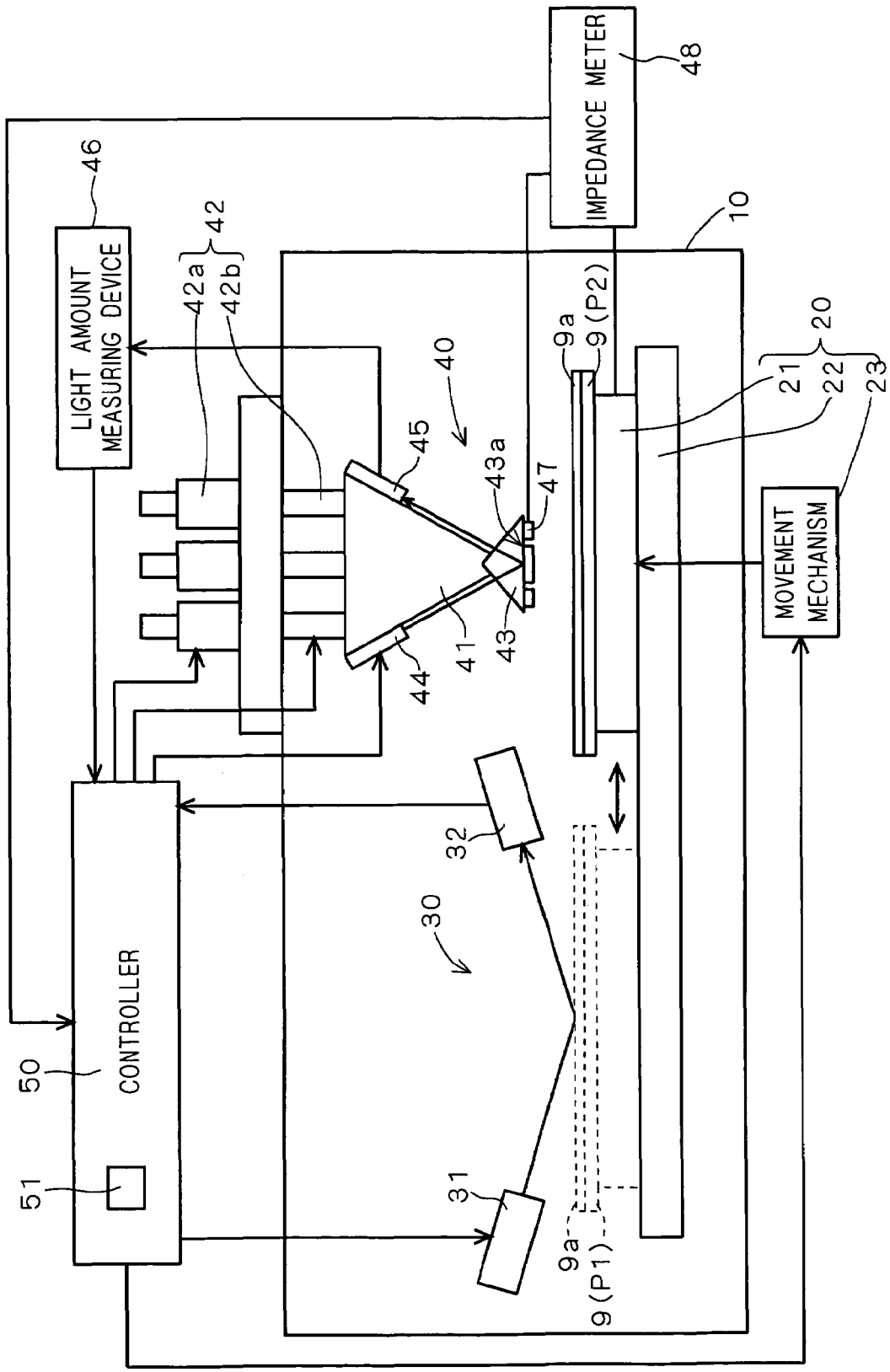
FIG. 1 shows the structure of a relative-dielectric-constant measuring apparatus.

FIG. 1 shows the structure of a relative-dielectric-constant measuring apparatus 1 according to the preferred embodiment of the present invention. The relative-dielectric-constant measuring apparatus 1 is an apparatus for measuring a relative dielectric constant $\in_{ins}$ of an insulation film 9a formed on the upper surface of a wafer (semiconductor substrate) 9. The relative-dielectric-constant measuring apparatus 1 includes a chamber 10, inside of which an ellipsometer 30 and a capacitance measuring part 40 are placed side by side. The ellipsometer 30 has the functions of both a film-thickness measuring part for measuring the film thickness of the insulation film 9a and an optical-constant measuring part for measuring the optical constants of the insulation film 9a. The relative-dielectric-constant measuring apparatus 1 further includes a loader 20 for carrying the wafer 9 between the ellipsometer 30 and the capacitance measuring part 40.

This relative-dielectric-constant measuring apparatus 1 can, using the ellipsometer 30, measure a film thickness dins and optical constants (refractive index, extinction coefficient) n and k of the insulation film 9a formed on the upper surface of the wafer 9. Also, the relative-dielectric-constant measuring apparatus 1 can, using the capacitance measuring part 40, measure a gap dair between a measuring electrode 47 provided in the capacitance measuring part 40 and the insulation film 9a and an accumulation capacitance Cacc. Then, the relative-dielectric-constant measuring apparatus 1 can calculate the relative dielectric constant $\in_{ins}$ of the insulation film 9a from the measured film thickness dins, the measured gap dair, and the measured accumulation capacitance Cacc.

Hereinbelow, the structures of the loader 20, the ellipsometer 30, and the capacitance measuring part 40 in the relative-dielectric-constant measuring apparatus 1 are respectively described first, and then the measurement procedure for the relative-dielectric-constant measuring apparatus 1 is described.

<2. Loader 20>

The loader 20 carries the wafer 9 between a measurement position P1 in the ellipsometer 30 and a measurement position P2 in the capacitance measuring part 40. The loader 20 includes a holder 21 for holding the wafer 9 almost horizontally; a rail 22 for supporting and guiding the holder 21 almost horizontally and linearly; and a movement mechanism 23 for moving the holder 21 along the rail 22.

The holder 21 is, for example, vacuum-contacted on the bottom surface of the wafer 9 to hold the wafer 9. A portion of the holder 21 which contacts the bottom surface of the wafer 9 is formed of an electrical conductor and serves as a contact electrode during measurement of a capacitance C which will be described later. The movement mechanism 23 is electrically connected to a controller 50 and moves the holder 21 according to electric signals from the controller 50.

<3. Ellipsometer 30>

The ellipsometer 30 has the function of measuring the film thickness dins and optical constants n and k of the insulation film 9a through observation of changes in polarization of a measuring light that is reflected off the surface of the insulation film 9a (changes in phase difference and amplitude ratio between s- and p-polarized lights). The ellipsometer 30 primarily includes a measuring-light emitting part 31, a reflected-light receiving part 32, and the controller 50.

The measuring-light emitting part 31 emits a measuring light in a predetermined polarized state toward the surface of the wafer 9 located at the measurement position P1 (i.e., the wafer 9 shown by broken lines in FIG. 1). This measuring light is emitted according to drive signals from the controller 50. The measuring-light emitting part 31 includes, for example, a xenon lamp as a light source for a measuring light, an optical fiber as a waveguide for light, and a polarizer for polarizing a measuring light.

The reflected-light receiving part 32 receives a measuring light reflected off the surface of the insulation film 9a and converts received light information into electric signals. The reflected-light receiving part 32 includes, for example, an analyzer, a spectroscope for dispersing light received, and a light receiver for converting light into electric signals.

The controller 50 calculates the film thickness dins and optical constants n and k of the insulation film 9a through analysis (so-called fitting) of signals obtained by the reflected-light receiving part 32, using prescribed equations based on optical models. The controller 50 includes, for example, a personal computer.

In the ellipsometer 30, a measuring light emitted from the measuring-light emitting part 31 enters the surface of the insulation film 9a on the wafer 9 located at the measurement position P1 at a predetermined angle of incidence (e.g., 75 degrees). Then, the reflected-light receiving part 32 receives and converts reflected light into electric signals, and the controller 50 calculates the film thickness dins and the optical constants n and k.

The ellipsometer 30 can, for example, be a so-called spectroscopic ellipsometer for conducting measurement using a plurality of measuring lights of different wavelengths. The use of a spectroscopic ellipsometer allows more accurate calculation of the film thickness dins and optical constants n and k of the insulation film 9a.

<4. Capacitance Measuring Part 40>

The capacitance measuring part 40 has the functions of measuring the gap dair between the wafer 9 located at the measurement position P2 (i.e., the wafer 9 shown by solid lines in FIG. 1) and the measuring electrode 47 and measuring a capacitance between the wafer 9 and the measuring electrode 47 for that gap dair. The capacitance measuring part 40 primarily includes a base 41, a base driver 42, a prism 43, a laser oscillator 44, a light receiving sensor 45, a light amount measuring device 46, the measuring electrode 47, an impedance meter 48, and the controller 50. At the measurement position P2, the holder 21 of the loader 20 is also a component of the capacitance measuring part 40 as a contact electrode.

Of the components of the capacitance measuring part 40, the prism 43, the laser oscillator 44, the light receiving sensor 45, the light amount measuring device 46, and the controller 50 serve as a gap measuring part for measuring the gap dair. On the other hand, the holder 21, the measuring electrode 47, the impedance meter 48, and the controller 50 serve as an accumulation-capacitance measuring part for measuring the accumulation capacitance Cacc which will be described later. Hereinbelow, each of the components will be described in detail.

The base 41 is a member for securely fastening the prism 43, the laser oscillator 44, and the light receiving sensor 45 thereto so as to keep their relative positions constant. The upper surface of the base 41 is coupled to the base driver 42. Actuation of the base driver 42 can lead to vertical and integral displacement of the base 41 as well as the prism 43, the laser oscillator 44, the light receiving sensor 45, and the measuring electrode 47, all of which are secured to the base 41. The base driver 42 includes a stepping motor 42a and a piezoelectric actuator 42b. Thus, for adjustment of the displacement of the base 41, coarse adjustment by the stepping motor 42a is followed by fine adjustment by the piezoelectric actuator 42b. This allows high-speed and high-precision displacement adjustment. The piezoelectric actuator 42b includes, for example, piezoelectric elements of lead zirconate titanate (PZT).

The prism 43 is an optical member for completely reflecting a laser beam emitted from the laser oscillator 44 and guiding it to the light receiving sensor 45. The prism 43 is secured to the base 41 in such a position that its one surface 43a forming a side face is nearly horizontal, facing downward (that is, in such a position that the surface 43a is parallel to the upper surface of the insulation film 9a). This surface 43a is a reflecting surface for laser beam. Hereinafter, the surface 43a is referred to as the bottom surface 43a.

The laser oscillator 44, according to drive signals from the controller 50, emits a laser beam such as a GaAlAs laser toward the bottom surface 43a. The laser beam emitted from the laser oscillator 44 is completely reflected off the bottom surface 43a of the prism 43 and received by the light receiving sensor 45. The light receiving sensor 45 is a light receiving element such as a photodiode and is connected to the light amount measuring device 46. The light amount measuring device 46 can measure the amount of the laser beam received by the light receiving sensor 45.

When the laser beam emitted from the laser oscillator 44 is completely reflected off the bottom surface 43a of the prism 43, the least amount of light will pass downwardly through the bottom surface 43a as an evanescent wave (so-called tunneling). Thus, the amount of light measured by the light amount measuring device 46 is a value that reflects this tunneling of the laser beam. Accordingly, the gap dair between the wafer 9 and the measuring electrode 47 can be determined based on the amount of light measured by the light amount measuring device 46.

Details of the principle of determining the gap dair from the amount of light measured by the light amount measuring device 46 has been disclosed, for example in Japanese Patent Application Laid-open No. 4-132236 (1992). More specifically, in given cases, a logarithm logRt of a transmittance Rt of a laser beam at the bottom surface 43a can be considered proportional to the gap dair. In this case, the amount of light emitted from the laser oscillator 44 and the amount of light measured by the light amount measuring device 46 are compared to obtain the reflectivity of a laser beam at the bottom surface 43a and then to obtain the transmittance Rt from the reflectivity. Thereby, the gap dair can be determined by proportional calculation. Application of such proportional calculation in determining the gap dair only requires relatively simple calculation, thus bringing the advantages of reduced calculation load on the controller 50 and improved measurement speed.

On the other hand, if more accuracy is required in determining the relationship between the logarithm logRt of the transmittance Rt and the gap dair, an accurate gap dair can be obtained by solving Maxwell's equations using as a boundary condition a four-layered structure consisting of the prism 43, an air space between the prism 43 and the insulation film 9a, the insulation film 9a, and the wafer 9.

Calculation conditions required in this case are optical constants of each layer. As the optical constants n and k of the insulation film 9a, the values measured by the ellipsometer 30 can be used. The optical constants of the prism 43, the air space, and the wafer 9 can all be generally known values. If the optical constants n and k of the insulation film 9a are known, those values may be used.

When the optical constants n and k of the insulation film 9a measured by the ellipsometer 30 are used for calculation of the gap dair, a laser beam from the laser oscillator 44 and a measuring light in the ellipsometer 30 should desirably be of the same wavelength. This is because, since the optical constants n and k depend on the wavelength of light, a more accurate gap dair can be calculated if the optical constants n and k for the measuring light in the ellipsometer 30 and those for the laser beam in the capacitance measuring part 40 are made equal to each other. Even when known values are used as the optical constants n and k of the insulation film 9a, it is desirable for the same reason to use the optical constants n and k corresponding to the wavelength of the laser beam from the laser oscillator 44.

The controller 50 performs the aforementioned calculations based on measurement signals received from the light amount measuring device 46, thereby to obtain the gap dair. At this time, the controller 50 serves as a part for calculating the gap dair based on the amount of light measured by the light amount measuring device 46.

The measuring electrode 47 is secured to the bottom surface 43a of the prism 43 and spaced as opposed to the insulation film 9a on the wafer 9 located at the measurement position P2. At this time, the measuring electrode 47 is secured to an area of the bottom surface 43a of the prism 43 which is away from the neighborhood of the reflecting point of the laser beam. This is to prevent cut-off of the aforementioned evanescent wave.

The measuring electrode 47 and the holder 21 of the loader 20 are both electrically connected to the impedance meter 48. The impedance meter 48 can apply a bias voltage V between the measuring electrode 47 and the holder 21 and can perform a so-called C-V measurement in which the capacitance C between the measuring electrode 47 and the holder 21 is measured with varying bias voltage V. The impedance meter 48 transmits the relationship between the bias voltage V and the capacitance C obtained through the C-V measurement, as electric signals, to the controller 50.

The controller 50 receives data on the bias voltage V and the capacitance C from the impedance meter 48 and determines from that data the accumulation capacitance Cacc between the holder 21 and the measuring electrode 47. The controller 50 then calculates the relative dielectric constant ∈ins of the insulation film 9a based on this accumulation capacitance Cacc, the aforementioned gap dair, and the film thickness dins of the insulation film 9a measured by the ellipsometer 30.

<5. Measurement Procedure>

Next described is the procedure for measuring the relative dielectric constant ∈ins of the insulation film 9a formed on the upper surface of the wafer 9 using the relative-dielectric-constant measuring apparatus 1.

Figure 2:
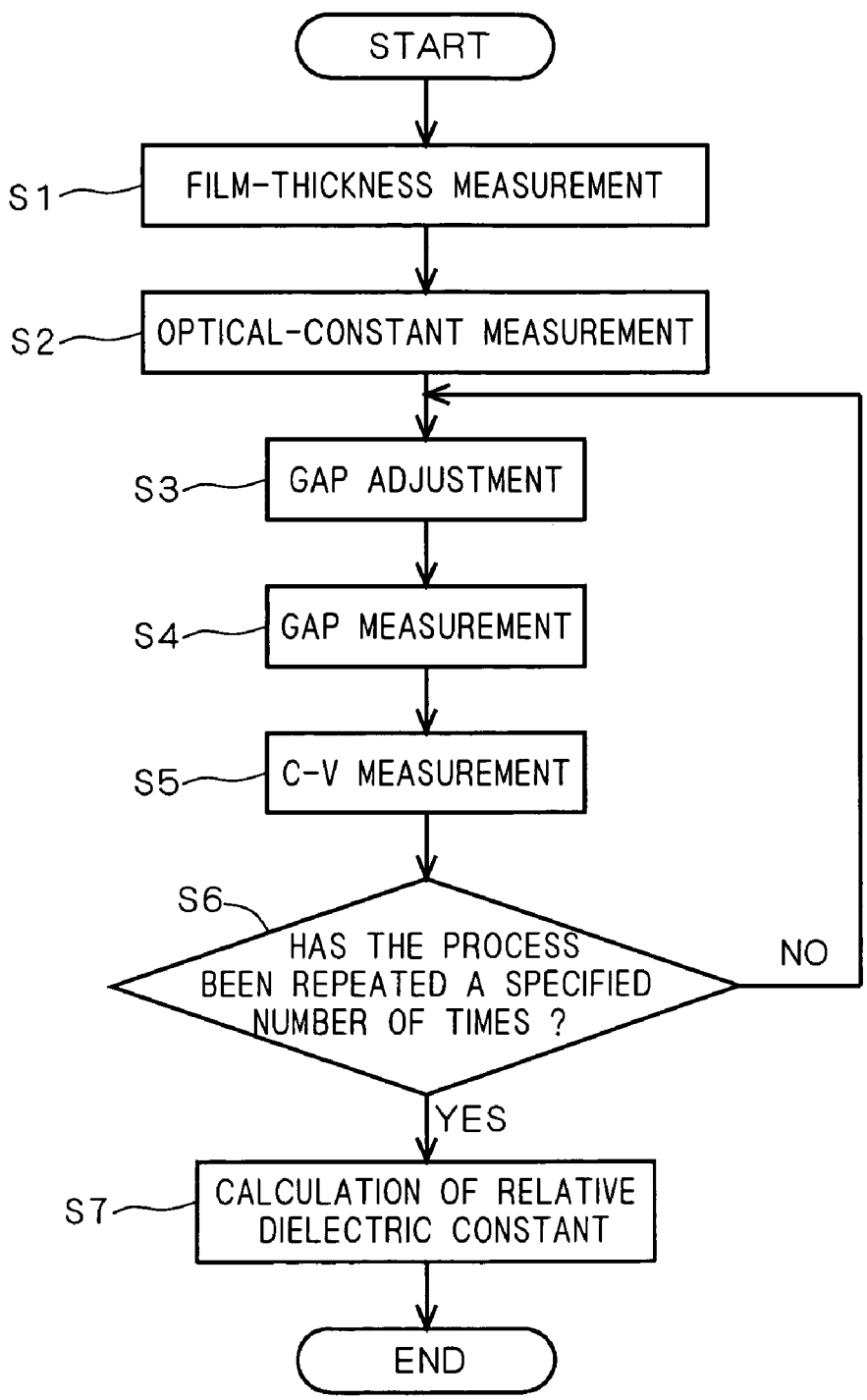
FIG. 2 is a flow chart illustrating the procedure for measurement of relative dielectric constant.

FIG. 2 is a flow chart illustrating the procedure for measuring the relative dielectric constant ∈ins with the relative-dielectric-constant measuring apparatus 1. The controller 50 stores a program 51 for performing this measurement procedure. The measuring operation proceeds with the controller 50 controlling the operations of the respective devices according to the program 51.

In the measurement of the relative dielectric constant ∈ins of the insulation film 9a, the wafer 9 is first held on the holder 21 of the loader 20 with its surface, on which the insulation film 9a is formed, facing upward. Then, the movement mechanism 23 moves the wafer 9 together with the holder 21 to the measurement position P1 in the ellipsometer 30.

With arrival of the wafer 9 at the measurement position P1, the measuring-light emitting part 31 emits a measuring light. The measuring light emitted enters the surface of the insulation film 9a at a predetermined angle of incidence, and its reflected light is received by the reflected-light receiving part 32. The reflected-light receiving part 32 converts the intensity of the received light into electric signals and transmits them to the controller 50. The controller 50 calculates the film thickness dins and optical constants n and k of the insulation film 9a by ellipsometry based on information on the electric signals received (steps S1 and S2).

Then, the movement mechanism 23 moves the wafer 9 together with the holder 21 to the measurement position P2 in the capacitance measuring part 40.

In the capacitance measuring part 40, the base driver 42 displaces the base 41, the prism 43, the measuring electrode 47, and the like integrally and adjusts their vertical positions. This adjusts the gap dair between the insulation film 9a on the wafer 9 located at the measurement position P2 and the measuring electrode 47 (step S3).

Then, the laser oscillator 44 emits a laser beam. The laser beam emitted is reflected off the bottom surface 43a of the prism 43 and received by the light receiving sensor 45. The amount of the laser beam is measured by the light amount measuring device 46. The light amount measuring device 46 transmits the measured amount of light as electric signals into the controller 50. The controller 50, according to the received amount of light, measures the gap dair between the measuring electrode 47 and the insulation film 9a (step S4).

In steps S3 and S4, the adjustment of the gap dair may be made by measuring (monitoring) the gap dair.

Thereafter, a C-V measurement for that gap dair is performed. More specifically, the impedance meter 48 applies the bias voltage V between the holder 21 and the measuring electrode 47 and, while varying the voltage value, measures the capacitance C between the holder 21 and the measuring electrode 47 for each bias voltage V (step S5). This C-V measurement is performed by observing charge movement while keeping the measuring electrode 47 away from the insulation film 9a. Thus, the C-V measurement is performed on the insulation film 9a without contact.

Figure 3:
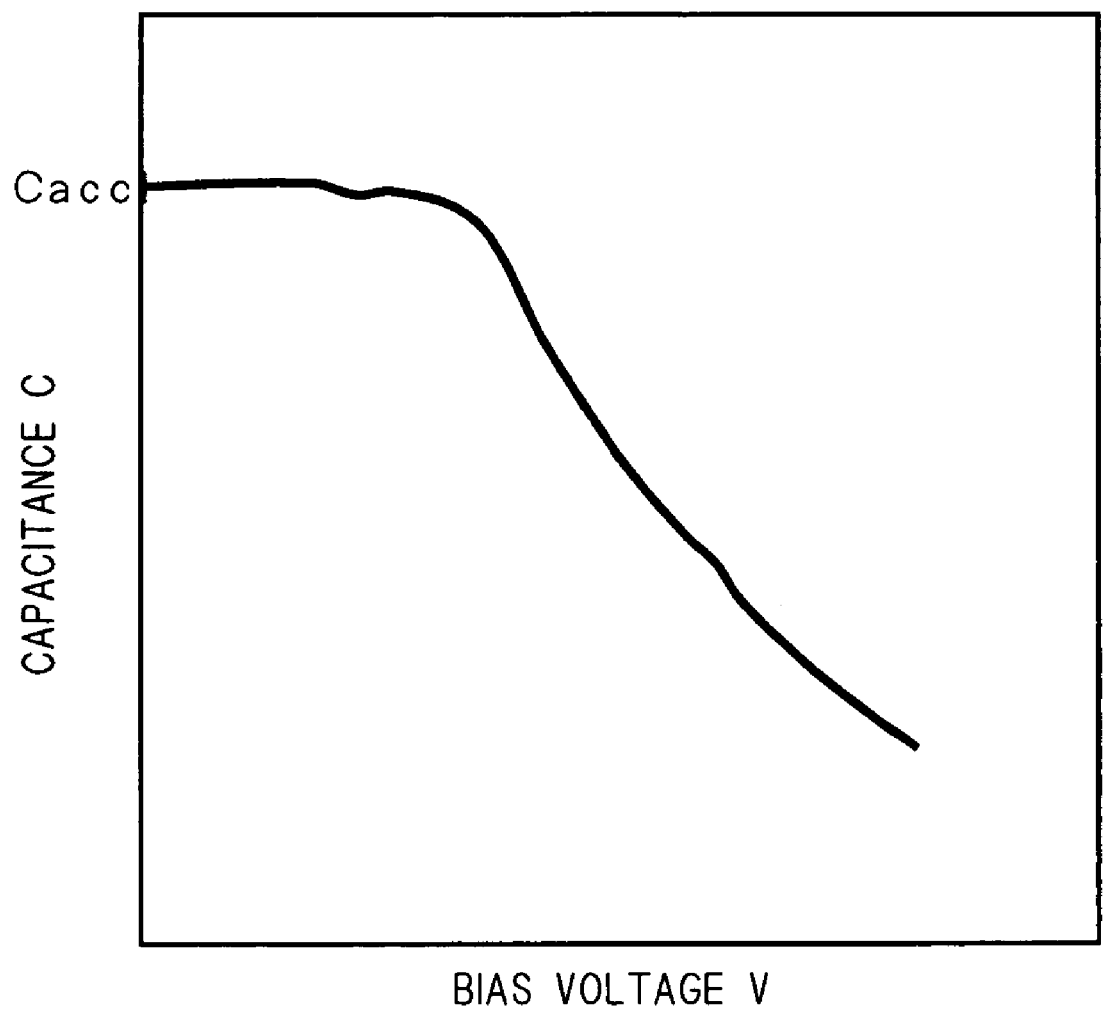
FIG. 3 is a graph showing an example of a C-V curve.

The C-V measurement in step S5 yields a C-V curve showing the relationship between the bias voltage V and the capacitance C for one gap dair. FIG. 3 is a graph showing an example of the C-V curve obtained in this way. The maximum value of the capacitance C (hereinafter referred to as the "accumulation capacitance Cacc") in this C-V curve will be used in the following calculations. This is because the maximum value of the capacitance C is the most suitable value for an approximate expression $C = \in S/d$ used in the following calculations.

The controller 50 receives, as electric signals, data on the bias voltage V and the capacitance C from the impedance meter 48. Then, the controller 50 calculates the accumulation capacitance Cacc based on the above C-V curve.

After the C-V measurement (step S5), the controller 50 determines whether the process from step S3 to step S5 has been repeated a specified number of times (step S6). If the number of iterations is less than the specified number of iterations, the process returns to step S3 to repeat the process from step S3 to step S5 with a different gap dair. If the number of iterations has reached the specified number of iterations, the process proceeds to the next step S7. In this fashion, the relative-dielectric-constant measuring apparatus 1 repeats the process from step S3 to step S5 a plurality of number of times with different gaps dair, and obtains a plurality of sets of measurement results of the gap dair and the accumulation capacitance Cacc for each gap dair.

It should be noted here that at least one set of the measurement results of the gap dair and the accumulation capacitance Cacc is necessary to obtain for calculation of a unique relative dielectric constant ∈ins of the insulation film 9a. Thus, at least a single execution of the process from step S3 to step S5 can achieve the object of the present invention. The purpose of repeating those steps is to calculate a more accurate relative dielectric constant ∈ins.

As above described, the process from step S3 to step S5 may be repeated a specified number of times. Or, as another alternative, the calculation of step S7, which will be described later, may be performed in advance, and the process from step S3 to step S5 and then to step S7 may be repeated until the relative dielectric constant ∈ins obtained falls within a predetermined margin of error.

Finally, the controller 50 calculates the relative dielectric constant ∈ins of the insulation film 9a based on the film thickness dins of the insulation film 9a, the gap dair, and the accumulation capacitance Cacc which have been obtained by the aforementioned measurements (step S7). Hereinbelow, details of the calculation of step S7 is described.

Figure 4:
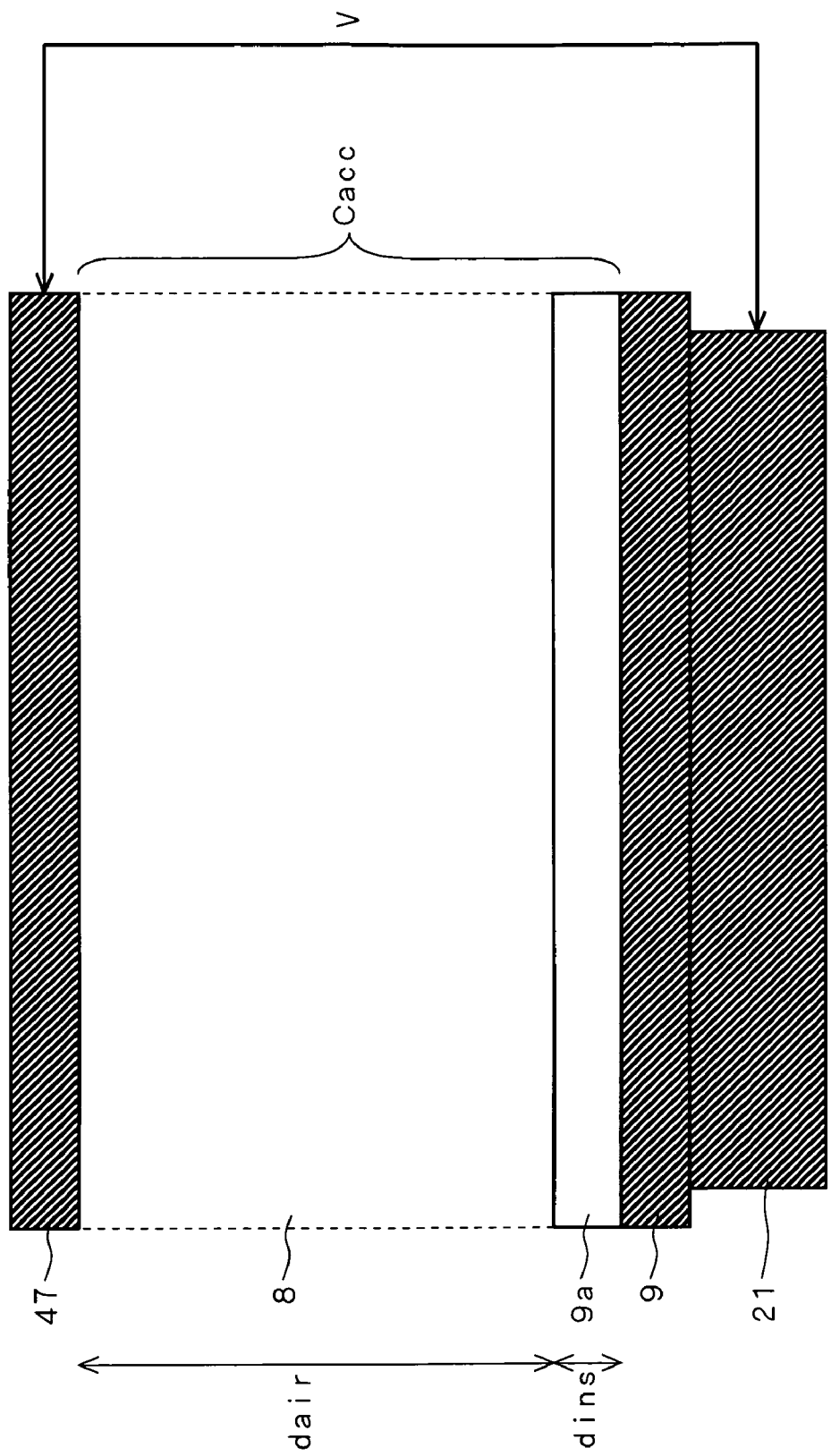
FIG. 4 is a schematic diagram showing the structure ranging from a measuring electrode to a holder.

As shown in FIG. 4, there exist the insulation film 9a and the air space 8 between the wafer 9 having continuity to the holder 21 and the measuring electrode 47. Thus, the accumulation capacitance Cacc obtained by the C-V measurement (step S5) is a resultant capacitance of the capacitance Cins of the insulation film 9a (hereinafter referred to as an "insulation capacitance") and the capacitance Cair of the air space 8 (hereinafter referred to as a "gap capacitance"). That is, the relationship among the accumulation capacitance Cacc, the insulation capacitance Cins, and the gap capacitance Cair can be expressed by the following equation (1):

$$\frac{1}{Cacc} = \frac{1}{Cair} + \frac{1}{Cins} \quad (1)$$

Since $Cair = \epsilon_o S/dair$ and $Cins = \epsilon_o \epsilon ins S/dins$ in equation (1), the following equation (2) is obtained:

$$\frac{1}{Cacc} = \frac{dair}{\epsilon_o S} + \frac{dins}{\epsilon_o \epsilon ins S} \quad (2)$$

where $\epsilon_o$ is the dielectric constant of vacuum, and S is the area of the measuring electrode 47.

In equation (2), the dielectric constant $\epsilon_o$ of vacuum and the area S of the measuring electrode 47 are known values. The values of the film thickness dins of the insulation film 9a, the gap dair, and the accumulation capacitance Cacc have already been obtained in the aforementioned steps S1, S3, and S5, respectively. That is, all the values except the relative dielectric constant $\epsilon ins$ of the insulation film 9a can be assigned. Accordingly, the relative dielectric constant $\epsilon ins$ can uniquely be calculated.

However, this relative-dielectric-constant measuring apparatus 1 acquires a plurality of sets of measured values of the gap dair and the accumulation capacitance Cacc by repetition of the process from step S3 to step S5. Thus, it is possible to calculate a more accurate relative dielectric constant $\epsilon ins$ of the insulation film 9a. The way of calculating a more accurate relative dielectric constant $\epsilon ins$ is as follows.

Figure 5:
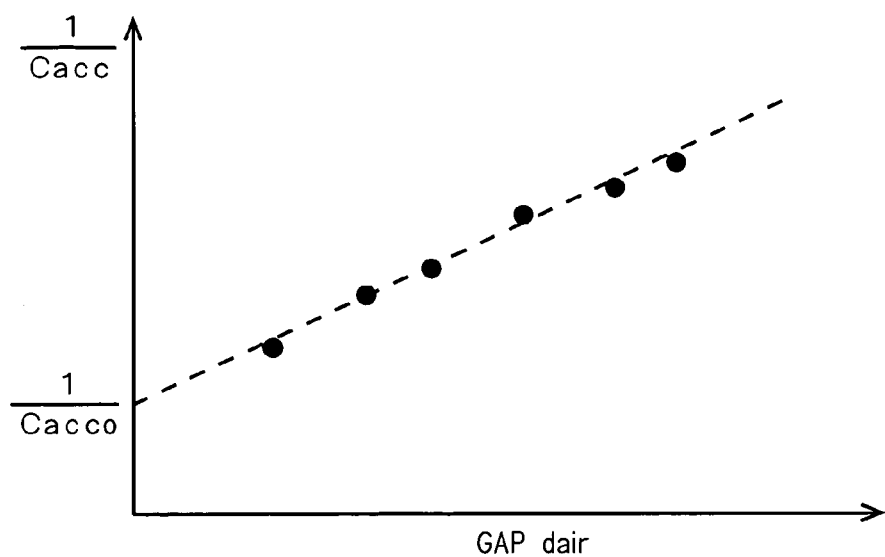
FIG. 5 is a graph plotting a reciprocal of an accumulation capacitance, and a gap.

In the above equation (2), the values 1/Cacc and dair are in proportional relationship where $\epsilon_o$, $\epsilon ins$, dins, and S are constant values. Thus, a graph as shown in FIG. 5 is obtained by plotting the reciprocal 1/Cacc of the accumulation capacitance Cacc and the gap dair obtained through steps S3 to S5. If the intercept on the vertical axis obtained by extrapolating this plot is 1/Cacco, this value corresponds to 1/Cacc where dair=0 in the above equation (2). Thus, substituting this intercept value 1/Cacco in the following equation (3) yields the relative dielectric constant $\epsilon ins$ of the insulation film 9a.

$$\epsilon ins = \frac{dins/\epsilon_o S}{1/Cacco} \quad (3)$$

The above intercept value 1/Cacco is derived from a set of data consisting of the gap dair and the accumulation capacitance Cacc. The film thickness dins obtained in step S1 is also substituted into the above equation (3). Thus, it can be said that this equation (3) also determines the relative dielectric constant $\epsilon ins$ based on the film thickness dins, the gap dair, and the accumulation capacitance Cacc. Further, known values should be assigned to the dielectric constant $\epsilon_o$ of vacuum and the area S of the measuring electrode 47.

The above intercept value 1/Cacco is the value obtained by extrapolating a plurality of plot data (a set of data consisting of 1/Cacc and dair). Thus, the relative dielectric constant $\epsilon ins$ calculated based on this intercept value 1/Cacco is more accurate than that calculated from a single set of data.

This relative-dielectric-constant measuring apparatus 1 can measure all of the above film thickness dins, optical constants n and k, gap dair, and accumulation capacitance Cacc without contact to the insulation film 9a. That is, non-destructive measurement of the wafer 9 is possible. Also, this relative-dielectric-constant measuring apparatus 1 does not require the process for forming an electrode on the surface of the insulation film 9a. This allows accurate measurement without altering the properties of the insulation film 9a. Further, since there is no need to apply charge to the surface of the insulation film 9a, no errors will occur in measured values due to a leakage current in the insulation film 9a.

<6. Examples>

Actual measurement of the relative dielectric constant $\epsilon ins$ of the insulation film 9a is made by this relative-dielectric-constant measuring apparatus 1. The insulation film 9a to be measured is formed of silicon oxide film with known optical constants n and k.

The film thickness dins of the insulation film 9a measured by the ellipsometer 30 is 111.5 nm.

Then, the capacitance measuring part 40 acquires sets of data each consisting of the gap dair and the reciprocal 1/Cacc of the accumulation capacitance Cacc. Plotting those data results in a graph as shown in FIG. 6.

Figure 6:
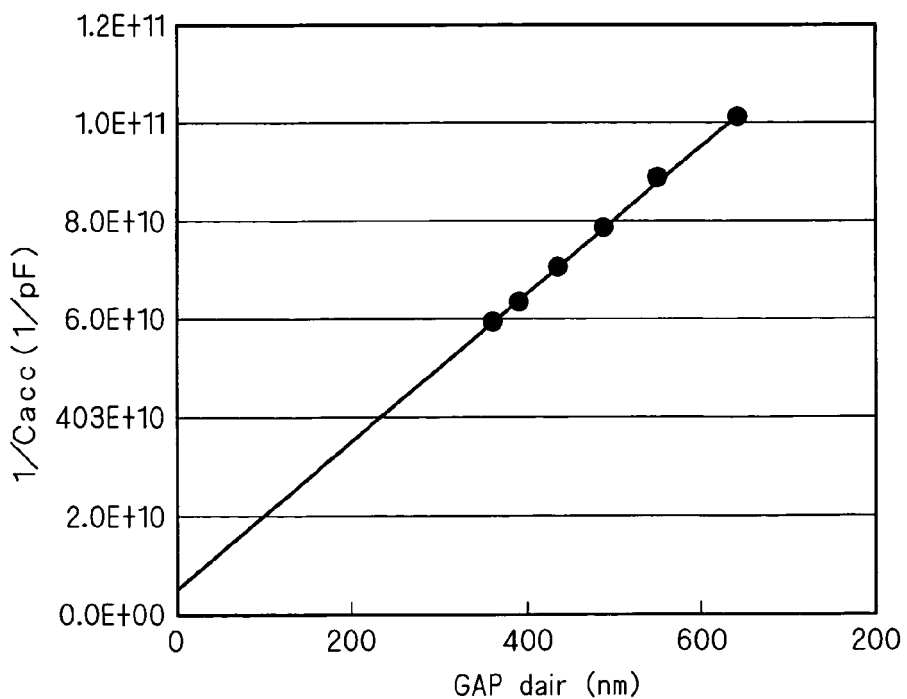
FIG. 6 is a graph plotting a reciprocal of a measured accumulation capacitance, and a measured gap.

When substituting the intercept value 1/Cacc obtained from the graph of FIG. 6, the above film thickness dins of 111.5 nm, the dielectric constant $\epsilon_o$ of vacuum of 8.854e-14F/m, and the area S of the measuring electrode 47 of 7.49e-7 $m^2$ into the above equation (3), we obtain the relative dielectric constant $\epsilon ins$ of 3.96 for the insulation film 9a.

This value is extremely close to a document relative dielectric constant value of 3.9 for silicon oxide film. This confirms that the relative-dielectric-constant measuring apparatus 1 can obtain the relative dielectric constant $\epsilon ins$ of the insulation film 9a with high precision.

<7. Alternatives>

Figure 7:
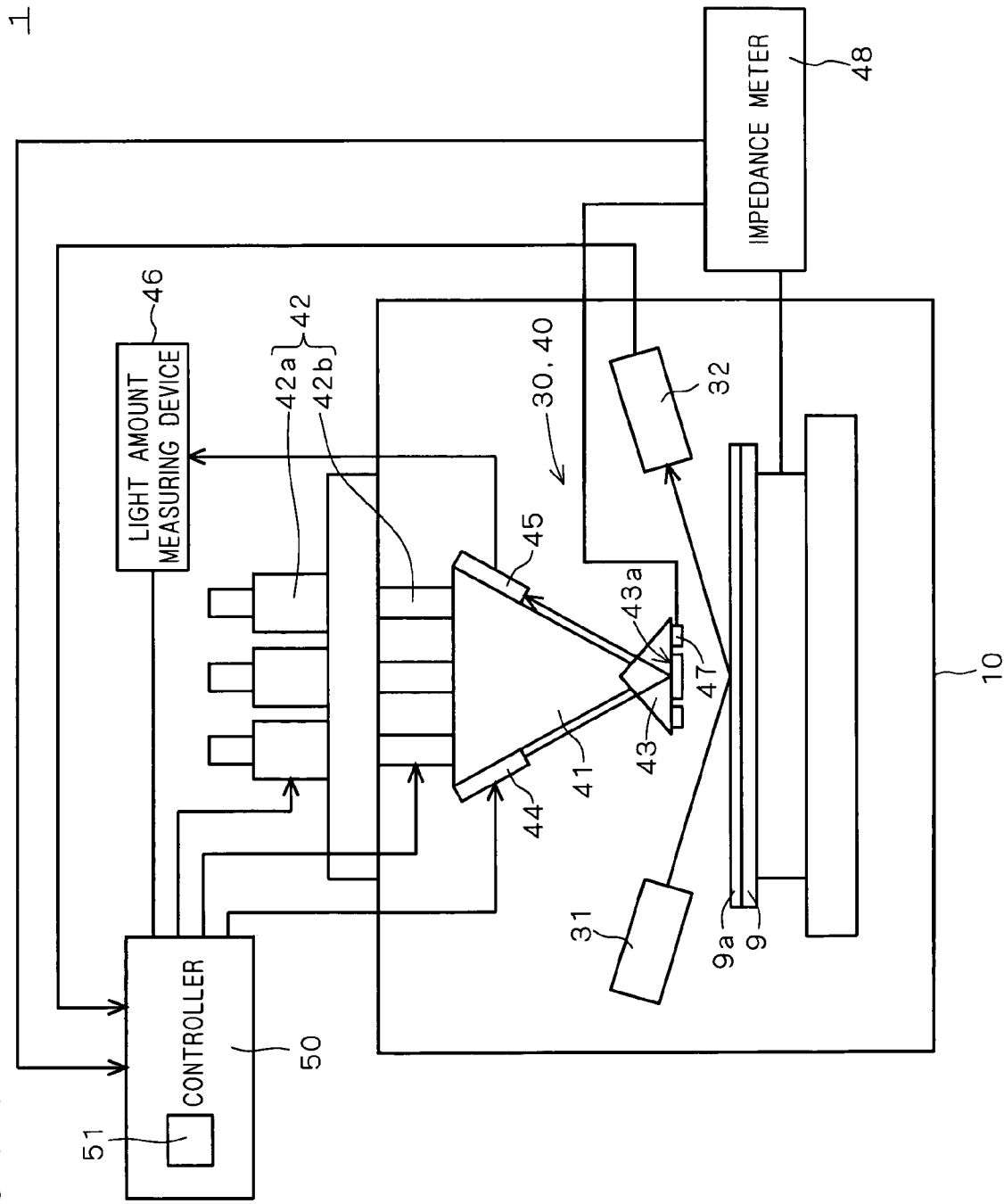
FIG. 7 shows the structure of a relative-dielectric-constant measuring apparatus excluding a loader.

The aforementioned relative-dielectric-constant measuring apparatus 1 includes the ellipsometer 30 and the capacitance measuring part 40 placed side by side. Thus, it is necessary to carry the wafer 9 between their measurement positions P1 and P2. Considering this point, the ellipsometer 30 and the capacitance measuring part 40 may be placed in such positions that they can measure the wafer 9 located at the same position as shown in FIG. 7. This eliminates the need to carry the wafer 9 by the loader 20, thus simplifying and minimizing the device structure. Besides, variations in measurement due to carrier error can be dissolved.

On the contrary, even if the ellipsometer 30 and the capacitance measuring part 40 are separate devices, the relative-dielectric-constant measuring method according to the present invention can be achieved with a measuring system that combines those devices.

The aforementioned relative-dielectric-constant measuring apparatus 1 performs measurements of the film thickness dins and the optical constants n and k by ellipsometry. However, those measurements may be performed using other non-contact measuring methods. For example, a measuring apparatus utilizing optical interference may be used.

While the invention has been shown and described in detail, the foregoing description is in all aspects illustrative and not restrictive. It is therefore understood that numerous modifications and variations can be devised without departing from the scope of the invention.

What is claimed is:

1. A relative-dielectric-constant measuring method for measuring a relative dielectric constant of an insulation film formed on a surface of a substrate, comprising the steps of:

(a) measuring a film thickness of said insulation film without contact;

(b) measuring a gap between said insulation film and an electrode spaced as opposed to said insulation film;

(c) measuring an accumulation capacitance between said substrate and said electrode; and (d) calculating the relative dielectric constant of said insulation film by assigning values of said film thickness measured in said step (a), said gap measured in said step (b), and said accumulation capacitance measured in said step (c) to an equation indicating a relation of said accumulation capacitance between said substrate and said electrode with a resultant capacitance of an insulation capacitance of insulation film and a gap capacitance of air space.

2. The relative-dielectric-constant measuring method according to claim 1, further comprising the step of:

(e) measuring optical constants of said insulation film without contact, wherein, in said step (b), said gap is measured based on said optical constants measured in said step (e).

3. The relative-dielectric-constant measuring method according to claim 2, wherein in said step (e), said optical constants of said insulation film are measured by ellipsometry.

4. The relative-dielectric-constant measuring method according to claim 3, wherein in said step (b), said gap is measured based on an amount of a laser beam that is completely reflected by an optical member to which said electrode is secured, and said ellipsometry in said step (e) uses a measuring light of the same wavelength as said laser beam.

5. The relative-dielectric-constant measuring method according to claim 4, wherein in said step (a), said film thickness of said insulation film is measured by ellipsometry.

6. The relative-dielectric-constant measuring method according to claim 5, further comprising the step of:

(f) adjusting said gap, wherein said steps (f), (b), and (c) are repeated a plurality of number of times to obtain a plurality of sets of measurement results of said gap and said accumulation capacitance, and in said step (d), said relative dielectric constant of said insulation film is calculated based on said plurality of sets of measurement results.

7. A relative-dielectric-constant measuring apparatus for measuring a relative dielectric constant of an insulation film formed on one surface of a substrate, comprising:

a film-thickness measuring part for measuring a film thickness of said insulation film without contact;

a capacitance measuring part for measuring a gap between said insulation film and a measuring electrode which is spaced as opposed to said insulation film and for measuring an accumulation capacitance between said substrate and said measuring electrode; and an operation part for calculating said relative dielectric constant of said insulation film by assigning values of said film thickness measured by said film-thickness measuring part, and said gap and said accumulation capacitance both measured by said capacitance measuring part to an equation indicating a relation of said accumulation capacitance between said substrate and said electrode with a resultant capacitance of an insulation capacitance of insulation film and a gap capacitance of air space.

8. The relative-dielectric-constant measuring apparatus according to claim 7, wherein said capacitance measuring part includes:

a contact electrode in contact with the other surface of said substrate;

said measuring electrode spaced as opposed to said insulation film on said substrate which is in contact with said contact electrode; an impedance meter for applying a bias voltage between said contact electrode and said measuring electrode, varying said bias voltage, and measuring a capacitance between said contact electrode and said measuring electrode.

9. The relative-dielectric-constant measuring apparatus according to claim 8, further comprising: an optical-constant measuring part for determining optical constants of said insulation film.

10. The relative-dielectric-constant measuring apparatus according to claim 9, wherein said optical-constant measuring part is an ellipsometer.

11. The relative-dielectric-constant measuring apparatus according to claim 10, wherein said capacitance measuring part measures said gap based on an amount of a laser beam that is completely reflected by an optical member to which said measuring electrode is secured, and said ellipsometer uses a measuring light of the same wavelength as said laser beam.

12. The relative-dielectric-constant measuring apparatus according to claim 11, wherein said film-thickness measuring part is an ellipsometer.

13. The relative-dielectric-constant measuring apparatus according to claim 12, wherein said capacitance measuring part further includes a gap adjusting part for adjusting said gap between said insulation film and said measuring electrode.

* * * * *